United States Patent [19]

Forrer et al.

[11] 4,308,347
[45] Dec. 29, 1981

[54] DEVICE FOR DETECTING MICROORGANISMS

[75] Inventors: Hans Forrer, Basel, Switzerland; Hans-Günther Zeller, Rheinfelden, Fed. Rep. of Germany

[73] Assignee: Hoffmann-La Roche Inc., Nutley, N.J.

[21] Appl. No.: 195,900

[22] Filed: Oct. 10, 1980

Related U.S. Application Data

[63] Continuation of Ser. No. 879,560, Feb. 21, 1978, abandoned.

[30] Foreign Application Priority Data

Feb. 18, 1977 [CH] Switzerland ................... 2063/77

[51] Int. Cl.³ .................... C12Q 1/04; C12M 1/24; C12M 1/16; C12M 1/18
[52] U.S. Cl. .................................. 435/34; 435/30; 435/296; 435/299; 435/300; 435/301; 141/319; 141/364; 206/219; 215/10
[58] Field of Search ............ 206/219; 215/10; 141/319, 320, 321, 322, 362, 363, 364, 365, 366; 128/272.1, 272.3, 218 M; 435/29, 30, 32, 33, 34, 296, 299, 300, 301

[56] References Cited

U.S. PATENT DOCUMENTS

| | | | |
|---|---|---|---|
| 2,773,521 | 12/1956 | Persson | 141/364X |
| 2,992,974 | 7/1961 | Belcone et al. | 435/206 X |
| 3,156,272 | 11/1964 | Indrunas | 215/10 X |
| 3,249,504 | 5/1966 | Cappel et al. | 435/240 |
| 3,261,381 | 7/1966 | Roach | 206/219 X |
| 3,266,533 | 8/1966 | McHale | 215/10 X |
| 3,449,210 | 6/1969 | Rohde | 435/299 X |
| 3,589,983 | 6/1971 | Holderith et al. | 435/296 |
| 3,651,926 | 3/1972 | Elfast, Jr. | 435/296 X |
| 3,733,179 | 5/1973 | Guehler | 422/72 X |
| 3,783,104 | 1/1974 | Henshilwood et al. | 435/295 |
| 3,783,106 | 1/1974 | Henshilwood | 435/30 X |
| 3,857,423 | 12/1974 | Ronca, Jr. | 141/319 X |
| 3,890,202 | 6/1975 | Bergeron | 435/294 |
| 3,966,552 | 6/1976 | Papano et al. | 435/295 |
| 4,072,577 | 2/1978 | Hirshaut | 435/295 |

FOREIGN PATENT DOCUMENTS

1310664 10/1962 France .
2202158 5/1974 France .

OTHER PUBLICATIONS

Becton and Dickinson & Co. Advertising Brochure.

Primary Examiner—Robert J. Warden
Attorney, Agent, or Firm—Jon S. Saxe; George M. Gould; John B. Wilson

[57] ABSTRACT

A device for the detection of microorganisms in a fluid sample comprising a first container a liquid nutrient medium and a second container containing one or more solid nutrient media, said containers being detachably connected so that the media can be brought into contact, is disclosed. Also disclosed is a method of detecting microorganisms in a fluid sample comprising introducing a sample of the fluid to be tested into a first container containing a liquid medium and incubating if desired; connecting said first container to a second container containing one or more solid media so that said media can be brought into contact; bringing the liquid and solid media into contact; incubating and determining the growth of microorganisms on the surface of the solid media.

12 Claims, 5 Drawing Figures

4,308,347

DEVICE FOR DETECTING MICROORGANISMS

This is a continuation, of application Ser. No. 879,560 filed Feb. 21, 1978 now abandoned.

BACKGROUND OF THE INVENTION

The present invention relates to the detection of microorganisms in a fluid sample such as, for example, body fluids.

The detection of microorganisms in body fluids, particularly bacterial in blood, requires that a sample of the fluid be used to inoculate a liquid nutrient medium. Subsequently, the liquid medium is in turn used to inoculate a solid medium to continue the growth of the organisms. For years, there have been in use detection systems in which both liquid and solid culture media are combined in the same container. Such systems avoid the troublesome and sometimes hazardous transfer of the precultures, i.e., the liquid medium, to the solid culture medium outside the container.

Such devices, i.e., those combining the liquid and solid media in a single container are not satisfactory for many reasons. In particular, because of the hazards inherent in constituents of the solid medium dissolving into the liquid medium, only solid media compatible with the liquid medium can be utilized. One of the major disadvantages of solid media constituents passing into the liquid media is that, when it occurs, differentiations of the pathogens may no longer be possible.

The solutions suggested to date for separating solid and liquid culture media are complicated, time-consuming, costly and/or facilitate separation of the media only during incubation, but not during tranport.

The above disadvantages of prior art methods are overcome in accordance with the present invention which provides a device whereby solid and liquid culture media are transported separately to the user or to a place of further processing after inoculation. The device of the present invention, however, provides for inoculation of the solid nutrient medium with the liquid medium as in conventional double culture bottles, i.e., by simply shaking and flooding the surface of the solid medium with the liquid medium.

SUMMARY OF THE INVENTION

In accordance with the present invention, a device for the detection of microorganisms in body fluids is provided which avoids the above-discussed disadvantages of the prior art. The subject device consists of two detachably connectable containers, one of which contains solid nutrient medium and the other liquid nutrient medium. The two containers are connectable with a common opening so that the media contained therein may be brought into contact.

The container as described above which contains the solid media is considered novel and consists of a tube having closure means at both ends, one of said closure means having affixed thereto a carrier protruding into the tube, said carrier being coated with one or more solid nutrient media. Preferably, the carrier is in the general shape of a microscope slide which may be coated on one or both sides with nutrient media. This container as well as the carrier and first container are of a transparent material such as glass or plastic, preferably the latter.

Further details and features of the invention will become apparent from the following detailed description and drawings, disclosing what is presently contemplated as being the best mode of the invention.

THE DRAWINGS

DETAILED DESCRIPTION OF THE INVENTION

Figure 4:
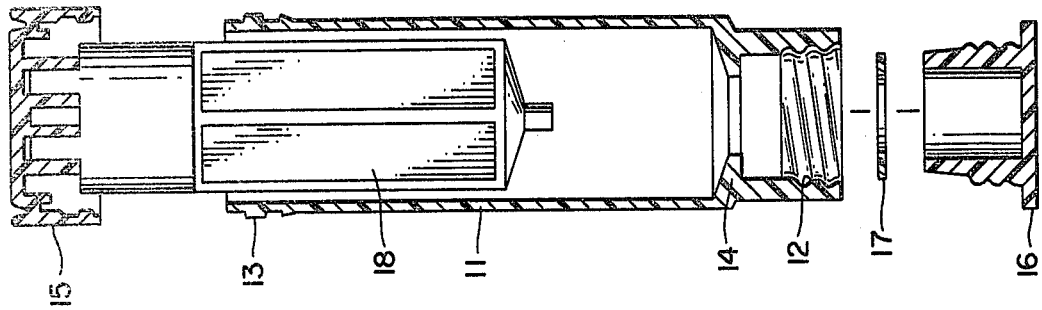
FIG. 4 is a partially exploded view of the container shown in FIG. 3.

Referring to the drawings:

The first container 1 consists of a flask 2 preferably of a transparent material, e.g., plastic or glass. The flask 2 is closed by a stopper 6, preferably of rubber, which can be pierced by a needle to introduce a fluid sample such as, for example, blood. The stopper 6 is pinched in a cap 4, preferably metal, which screws onto the flask 2 so that, when the cap 4 is removed, the stopper 6 is automatically entrained. The cap 4 has a removable part 5 so that a needle can pierce the stopper 6 without difficulty. The container 1 contains a liquid culture medium 7 preferably under a carbon dioxide atmosphere and a partial vacuum.

Figure 2:
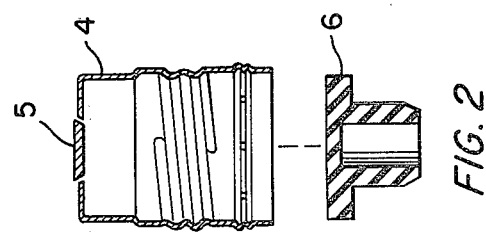
FIG. 2 is an exploded view of the cap assembly of the container shown in FIG. 1.

FIG. 2 shows more detail regarding the stopper 6 and the removable piece 5 in the cap 4.

Figure 3:
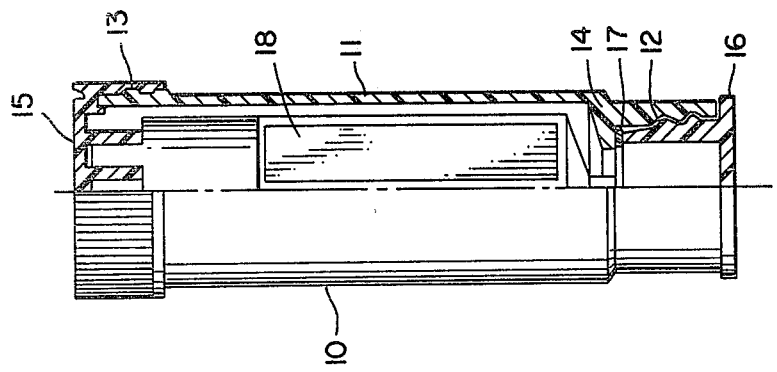
FIG. 3 is a longitudinal cross section of the second container in accordance with the present invention which contains one or more solid nutrient media.
Figure 1:
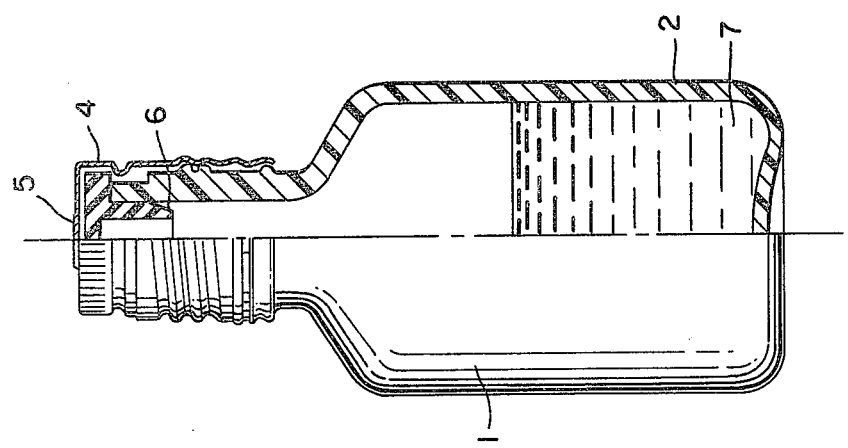
FIG. 1 is a longitudinal cross section of the first container in accordance with the present invention which contains liquid nutrient medium.

The second container 10 shown in FIG. 3 is a tube 11 of a transparent material such as plastic or glass having screw threading 12 on the inside of the cylindrical limit 14 of the bottom end and screw threading 13 on the outside of the upper end. The screw threading 12 corresponds to the threading present on the neck of the flask 2 as shown in FIG. 1 and permits connection of the two containers. The tube 11 is sealed at the bottom with a screw-on closure 16.

In order to achieve hermetic sealing of the two containers, the tube 11 is provided with a sealing ring 17 within the cylindrical limit 14 of the bottom of tube 11. This ring is preferably a material such as polyethylene. The tube 11 is provided with a seal 15 screwed onto the threading 13 at the upper end. A carrier, e.g., a slide 18, preferably of a transparent material such as glass or plastic, coated on one or both sides with one or more solid nutrient media is attached firmly to the seal 15.

FIG. 4 shows the container shown in FIG. 3 with the closure 16 and sealing ring 17 removed and the seal 15 with attached carrier 18 partially removed.

In use, a fluid sample such as blood is introduced into container 1 with the aid of a transfer instrument provided with a needle. To make the transfer, the removable part 5 of the cap 4 is removed so that the needle can be inserted through the stopper 6. The flow of the fluid into the flask is preferably enhanced by a partial vacuum in the flask.

After the desired amount of fluid has been introduced into the flask 2, the needle is removed whereby the stopper 6 reseals automatically. The flask may then be incubated at 20°–37° C. for from one hour up to about 10 days.

Figure 5:
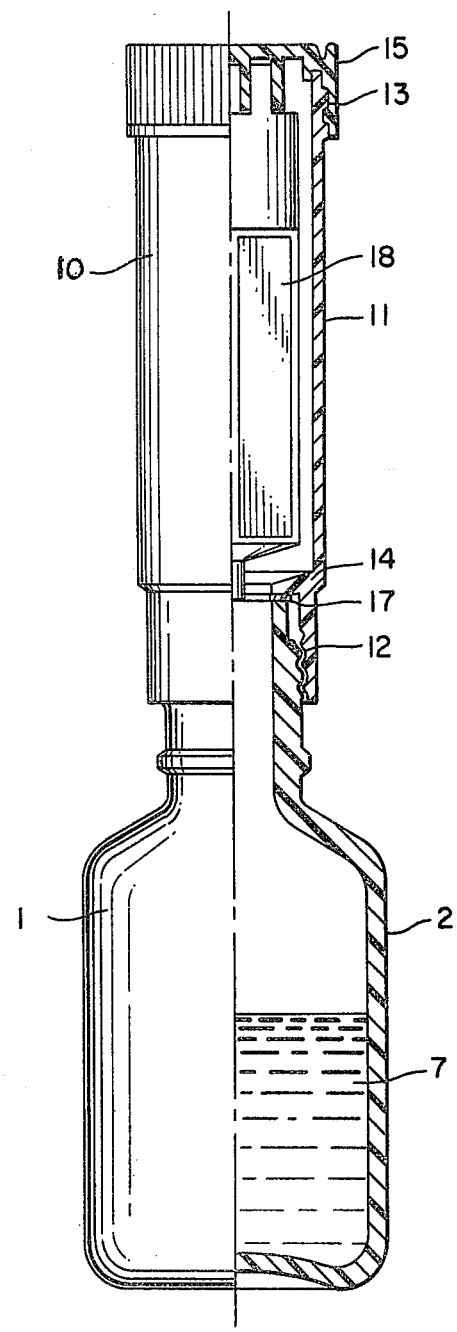
FIG. 5 is a cross sectional view of the device of the present invention formed by the combination of the containers shown in FIGS. 1 and 3.

After the incubation is complete, the cap 4 of flask 2 is removed, thus also removing stopper 6. The container 1 is then connected to container 10 by screwing it onto the lower end thereof which was opened by removing seal 16. FIG. 5 shows the two containers connected in this fashion.

The device thus-formed is then tilted several times to guarantee optimum contact between the liquid and the solid nutrient media. The apparatus is then incubated at 20°–37° C. for from one hour up to 10 days after which the growth present on the sodium medium is observed and evaluated. If no growth can be detected, the process can be repeated several times. In case of longer incubations, the apparatus is tipped at least once a day to guarantee optimum contact between the liquid and solid nutrient media.

It is to be understood that the present invention is in no way intended to be limited to the specific embodiment described above. For example, containers 1 and 10 can be of any convenient form and can be sealed in various ways readily apparent to the skilled artisan. For example, container 10 need not have a sealable opening at both ends and the solid media can be cast on the inside surface thereof instead of a carrier.

In addition, screw seals need not necessarily be used to seal the containers. They may be connected in other ways such as, for example, by insertion and locking. Also, the seals of the two containers may be designed in such a way that, when they are combined, the interiors are brought into contact without the necessity of removing two seals and opening of the containers.

The apparatus of the present invention facilitates detection of microogranisms in a fluid sample by the following:
(a) a sample of the fluid to be tested is introduced into a first container containing a liquid medium and optionally the mixture is incubated;
(b) the first container is connected to a second container containing one or more solid nutrient media to form an assembly having the interiors of the two containers in contact;
(c) the contents of the first container are brought into contact with the surface of the solid nutrient media in the second container;
(d) the assembly is then incubated; and
(e) the surface of the solid nutrient medium is examined for growth of microorganisms.

The incubation in step (a) of the above process is optional, i.e., the liquid medium can be utilized solely as a transport medium. However, the incubation of step (d) is necessary and can be carried out under either aerobic or anaerobic conditions. In the latter instance the seal 15 of the container 10 can be provided with openings for introducing an inert gas such as nitrogen or carbon dioxide and expelling air. The inert gas, particularly carbon dioxide, can be produced with the aid of a gas source present in the container with the solid nutrient medium or on the seal 15.

The present invention can be utilized to detect the presence of microogranisms such as bacteria, fungi, yeasts and the like in a fluid sample. Body fluids such as blood or urine are preferred.

The present invention is not intended to be limited to a single solid nutrient medium. It is within the scope of the invention to use two or more such media to facilitate identification of the microorganisms which might be present in the sample. Further, the culture media can contain antibiotics and/or other chemotherapeutic agents, to permit sensitivity testing of microorganisms.

We claim:

1. A device for the detection of microorganisms in a fluid sample comprising a first container containing a liquid nutrient medium and a second container containing one or more solid nutrient media, said containers being detachably connected to each other so as to confine by a detachable connection openings communicating both containers, thereby enabling the liquid medium to be brought into contact with the solid medium; said second container being a transparent tube having a closure means at an end other than where detachably connected to said first container; said closure means having affixed thereto a carrier protruding into and completely contained by said tube and coated with said one or more solid nutrient media; and said tube having another closure means for said end detachably connectable to said first container when first container is detached.

2. A device in accordance with claim 1 wherein said containers are detachably connected by a threaded connection.

3. A device in accordance with claim 1 wherein said second container contains a single nutrient medium.

4. A device in accordance with claim 1 wherein said second container contains two or more nutrient media.

5. A device according to claim 1 wherein said carrier is in the form of a microscope slide.

6. A device according to claim 5 wherein said slide is coated on both sides with solid nutrient media.

7. A method for the detection of microorganisms in a fluid sample comprising:
(a) introducing said sample into a liquid nutrient medium contained in a first container;
(b) connecting the first container to a second container having a closure means for one of two ends of the second container, the closure means having affixed thereto a carrier contained within the second container and coated with one or more solid nutrient media, the second container being connected at the other of said two ends to the first container so as to communicate both containers by a common opening, permitting thereby the liquid nutrient medium to be brought into contact with the solid nutrient medium;
(c) contacting the solid nutrient medium with the liquid nutrient medium;
(d) incubating the solid nutrient medium for a time suitable for growth of said microorganisms; and
(e) determining the growth of said microorganisms on the solid nutrient medium.

8. A method in accordance with claim 7 wherein the mixture of said liquid nutrient medium and said fluid sample is incubated for a certain time before said first container is connected to said second container.

9. A method in accordance with claim 7 wherein said second container contains at least two nutrient media.

10. A method in accordance with claim 7 wherein said fluid sample is blood.

11. A method in accordance with claim 7 wherein said first container and second container are detached after contacting the solid nutrient medium with the liquid nutrient medium.

12. A method in accordance with claim 11 wherein after detaching said first and second container, the said second container is closed by closure means at both ends.

* * * * *